(12) United States Patent
Mao et al.

(10) Patent No.: US 11,207,683 B2
(45) Date of Patent: Dec. 28, 2021

(54) METHOD AND ARRANGEMENT FOR FOCUSING OBJECTS IN A FLOW

(71) Applicants: IMEC VZW, Leuven (BE); Katholieke Universiteit Leuven, KU LEUVEN R&D, Leuven (BE)

(72) Inventors: Shengping Mao, Heverlee (BE); Erik Sohn, Leuven (BE); Xavier Rottenberg, Kessel-Lo (BE); Chengxun Liu, Kessel-Lo (BE)

(73) Assignees: IMEC vzw, Leuven (BE); Katholieke Universiteit Leuven, KU LEUVEN R&D, Leuven (BE)

( * ) Notice: Subject to any disclaimer, the term of this patent is extended or adjusted under 35 U.S.C. 154(b) by 408 days.

(21) Appl. No.: 16/322,820

(22) PCT Filed: Jul. 28, 2017

(86) PCT No.: PCT/EP2017/069186
§ 371 (c)(1),
(2) Date: Feb. 1, 2019

(87) PCT Pub. No.: WO2018/024639
PCT Pub. Date: Feb. 8, 2018

(65) Prior Publication Data
US 2019/0201901 A1    Jul. 4, 2019

(30) Foreign Application Priority Data
Aug. 2, 2016    (EP) .................................... 16182277

(51) Int. Cl.
*B01L 3/00* (2006.01)
*G01N 29/22* (2006.01)
(Continued)

(52) U.S. Cl.
CPC ..... *B01L 3/502761* (2013.01); *A61M 1/3678* (2014.02); *B01L 3/502746* (2013.01);
(Continued)

(58) Field of Classification Search
None
See application file for complete search history.

(56) References Cited

U.S. PATENT DOCUMENTS 5,853,994 A * 12/1998 Gopinathan ......... G01N 29/036
435/6.11
2006/0037915 A1    2/2006 Strand et al.
(Continued)

OTHER PUBLICATIONS

PCT International Search Report and Written Opinion, PCT International Application No. PCT/EP2017/069186, dated Oct. 16, 2017, 12 pages.

*Primary Examiner* — Matthew D Krcha
*Assistant Examiner* — Brittany I Fisher
(74) *Attorney, Agent, or Firm* — McDonnell Boehnen Hulbert & Berghoff LLP (57) ABSTRACT

At least one embodiment relates to a focusing arrangement for focusing particles or cells in a flow. The arrangement includes at least one channel for guiding the flow. The channel includes (i) at least one particle confinement structure having particle flow boundaries and (ii) at least one acoustic confinement structure having acoustic field boundaries adapted for confining acoustic fields. The acoustic field boundaries may be different from the particle flow boundaries, and the at least one acoustic confinement structure may be arranged with regard to the channel to at least partially confine acoustic fields in the channel.

19 Claims, 8 Drawing Sheets

(51) Int. Cl.
*G01N 15/14* (2006.01)
*G01N 15/00* (2006.01)
*A61M 1/36* (2006.01)

(52) U.S. Cl.
CPC ....... *G01N 15/1404* (2013.01); *G01N 29/222* (2013.01); *A61M 2205/0244* (2013.01); *B01L 2200/0652* (2013.01); *B01L 2300/0816* (2013.01); *B01L 2300/168* (2013.01); *B01L 2400/0436* (2013.01); *B01L 2400/0439* (2013.01); *B01L 2400/086* (2013.01); *B01L 2400/088* (2013.01); *G01N 2015/0053* (2013.01); *G01N 2015/0065* (2013.01); *G01N 2015/142* (2013.01)

(56) References Cited

U.S. PATENT DOCUMENTS

| | | | |
|---|---|---|---|
| 2006/0266692 A1 | 11/2006 | Foster et al. | |
| 2009/0226994 A1 | 9/2009 | Lemor et al. | |
| 2012/0269683 A1* | 10/2012 | Packirisamy | G02B 6/1225 422/82.11 |
| 2013/0214176 A1* | 8/2013 | Graves | G01N 15/1404 250/459.1 |

* cited by examiner

METHOD AND ARRANGEMENT FOR FOCUSING OBJECTS IN A FLOW

CROSS-REFERENCE TO RELATED APPLICATION

The present application is a national stage entry of PCT/EP2017/069186 filed Jul. 28, 2017, which claims priority to EP 16182277.0 filed on Aug. 2, 2016, the contents of each of which are hereby incorporated by reference.

FIELD OF THE DISCLOSURE

The invention present disclosure relates to the field of focusing structures for focusing small objects, such as particles or cells, in a flow. More specifically, it relates to focusing arrangements which are based on acoustic radiation forces.

BACKGROUND

For many microfluidic applications, flow focusing of particles or cells is an essential step for sample enrichment or separation. This is conventionally accomplished by hydrodynamic focusing using a sheath fluid to guide particles into the center of a channel. To generate a sufficient focusing effect on the particles, sheath fluid flow might sometimes be orders of magnitude greater than the flow of the sample fluid.

In conventional standing wave acoustophoresis systems, acoustic radiation forces are used to separate particles or cells from a liquid. In such systems, it is possible to separate particles or cells based on their size and density. The migration velocity of particles in standing wave acoustophoresis is proportional to the square of the particle radius, the frequency of the acoustic field and the square of the pressure amplitude.

In reality, however, it may be challenging to infinitely increase the frequency and the driving power, so as to increase the speed of focusing.

SUMMARY

The present disclosure provides an arrangement for focusing particles or cells in a flow.

The present disclosure is enabled, for example, by a method and arrangement according to the claims.

In a first aspect, the present disclosure relates to a focusing arrangement for focusing particles or cells in a flow. The arrangement includes at least one channel, and at least one acoustic confinement structure comprising acoustic field boundaries adapted for confining acoustic fields, at least partially, in the channel.

The channel includes at least one particle confinement structure including particle flow boundaries. The movement space of the particles is limited by these particle flow boundaries. The particle flow boundaries may for example be the walls of the channel or they may, for example, include one or more pillar arrays within the channel, which could help limit the free flow of the particles.

In embodiments of the present disclosure, the acoustic field boundaries are different from the particle flow boundaries.

Given the present disclosure, the efficiency of focusing particles can be improved. This is achieved by a focusing arrangement where the acoustic field boundaries are different from the particle flow boundaries.

Design of the acoustic confinement structures may, for example, be such that resonance conditions are satisfied, and/or such that specific pressure fields in the acoustic confinement structures can be obtained. The particles may, for example, be focused towards the center of the flow. Thus, a better and/or more efficient focusing of the particles in the flow in the channel may be obtained. For these designs, the acoustic field boundaries [[are]] may be different from the particle flow boundaries.

In some embodiments, focusing of particles or cells in parallel channels is enabled and/or focusing arrangements are scalable with regard to the number of channels.

In case particles or cells are flowing in parallel channels, the focusing of the particles in the flow is improved by design of the acoustic confinement structures. Hence, the resonance conditions of the acoustic confinement structures are tuned depending on the position on the chip. In an example embodiment, the acoustic confinement structures are designed, such that it may be possible to align particles synchronously in different channels. It may, for example, be possible to have a similar or even the same acoustic field distribution in the different channels. In embodiments of the present disclosure, it may also be avoided that the acoustic field of an acoustic confinement structure of a first channel is disturbing the focusing of the particles in the second channel. In example embodiments involving multi-channel focusing arrangements, a higher throughput can be achieved than when using only one channel.

In case particles are flowing in one channel through consecutive acoustic fields generated by consecutive acoustic confinement structures, the focusing of the particles in the flow is improved by designing the acoustic confinement structures depending on their position in the sequence. The first acoustic confinement structure may, for example, be designed such that in operation the acoustic field in this structure forces the particles away from the side walls of the channel. The second acoustic confinement structure may, for example, be designed such that in operation the acoustic field in this structure forces the particles to the center of the channel.

In embodiments of the present disclosure, the focusing arrangement includes two channels, where each channel includes an acoustic confinement structure adapted for confining acoustic fields, at least partially, in that channel.

In an example embodiment, each channel comprises an acoustic confinement structure, and the acoustic confinement structures are adapted for confining the acoustic field in the channel. This enables a design of the acoustic confinement structures that depends on their position in the focusing arrangement. The design of the acoustic confinement structure may, for example, define the resonance condition for the acoustic wave within the acoustic confinement structure.

In embodiments of the present disclosure, the acoustic confinement structure may be designed to obtain a specific amplitude and phase of the generated acoustic field. In embodiments of the present disclosure, cross-channel interference is compensated for when designing the acoustic confinement structures. In embodiments of the present disclosure, one or more of the acoustic confinement structures may each respectively include a generator for generating the acoustic field. In these embodiments, the focusing arrangement may be adapted for controlling the generators to control the acoustic fields with regard to each other.

In embodiments according to the present disclosure, the focusing arrangement comprises an acoustic barrier, where the acoustic barrier is present as the acoustic confinement structure.

In an example embodiment, the focusing arrangement includes an acoustic barrier to help avoid a situation where the acoustic field of one of the acoustic confinement structures interferes with the acoustic field of the other acoustic confinement structure. The acoustic barrier may prevent a situation where the acoustic field within the first acoustic confinement structure is disturbing the focusing of the particles in the second channel and vice versa. In this way, cross-channel interference might be reduced.

In embodiments according to the present disclosure, at least one acoustic confinement structure includes acoustic barriers adapted to reflect a travelling acoustic wave.

In embodiments of the present disclosure, the acoustic barrier of an acoustic confinement structure allows to define the resonance condition for the acoustic waves within the acoustic confinement structure. In embodiments of the present disclosure, the uniformity of the acoustic field may be improved by strengthening the resonance of one individual channel as a result of acoustic barriers, which will reduce or even make the coupling with the remaining part of the chip negligible.

In embodiments of the present disclosure, at least one channel includes two consecutive acoustic confinement structures.

In an example embodiment, the focusing of the particles in the flow can be improved by controlling the acoustic confinement structures with regard to each other. The first acoustic field may, for example, have control on the inlet of the focusing channel.

In embodiments of the present disclosure, the focusing arrangement includes a particle confinement structure adapted for restricting the flow of the particles in the channel. The particle confinement structure includes particle flow boundaries which may or may not be different from the channel walls. In embodiments of the present disclosure, the acoustic field boundaries are different from the particle flow boundaries.

In an example embodiment, the flow of the particles in the channel may be restricted. This may, for example, cause the particles to be moved away from the side wall of the channel. By moving away the particles from the side wall, they can be better focused by an acoustic confinement structure in a later stage in the channel. In some embodiments, the focusing of particles can be accelerated by shortening the migration path and increasing the force applied on the particles.

In embodiments according to the present disclosure, the particle confinement structure comprise includes a pillar array.

In an example embodiment, the pillar array may not disturbe the acoustic field or the liquid flow, and the pillar array may restrict the flow of the particles.

In embodiments of the present disclosure, the particle confinement structure comprise includes an acoustic transparent layer.

In an example embodiment, the particle flow may be restricted and the acoustic field might not be disturbed by the acoustic transparent layer. In embodiments according to the present disclosure, the channel walls may be polymer walls and the acoustic confinement structures may comprise include acoustic field boundaries to modify the resonance condition of the acoustic wave and improve the focusing effect on the particles.

The present disclosure also relates to a diagnostic device, which includes: a focusing arrangement according embodiments of the present disclosure, for focusing cells or bioparticles in a flow. The diagnostic device may, for example, include a module for determining a quality and/or quantity of the focused bioparticles or cells and for providing an output based thereon. A diagnosis can be based on the output.

The present disclosure also relates to an industrial inspection device for monitoring a liquid flow comprising cells or particles. The industrial inspection device includes: a focusing arrangement according to embodiments of the present disclosure, for focusing cells or particles in a flow. The industrial inspection device may, for example, include a module for determining a quality and/or quantity of the focused particles or cells and for providing an output based thereon, the output being for characterizing the liquid flow.

The present disclosure also relates to a method for focusing particles or cells in a flow. The method may involve limiting movement of the particles using particle flow boundaries, resulting in a confined flow of particles and may also involve focusing the particles in the confined flow of particles using an acoustic confinement structure including acoustic field boundaries, the acoustic field boundaries being different from the particle flow boundaries.

In embodiments according to the present disclosure, the particles in a first channel are focused by applying a first acoustic field and the particles in a second channel are focused using a second acoustic field.

In some embodiments, it is possible to focus particles in parallel channels.

In embodiments according to the present disclosure, the method may involve two steps for focusing particles consecutively in a channel by consecutive acoustic fields, where in a first step the particles are moved away from the channel wall by a first acoustic field, and where in a second step the particles are focused in the channel by a second acoustic field. In embodiments according to the present disclosure, the particles may, for example, be moved towards the center of the channel.

In embodiments according to the present disclosure, the method may involve a step for limiting the flow of the particles using particle flow boundaries different from the channel boundaries before focusing the particles using an acoustic field.

In embodiments according to the present disclosure, the flow of the particles is limited using a pillar array or using an acoustic transparent layer.

Aspects of the present disclosure are set out in the accompanying independent and dependent claims. Features from the dependent claims may be combined with features of the independent claims and/or with features of other dependent claims.

These and other aspects of the present disclosure will be apparent from and elucidated with reference to the embodiment(s) described hereinafter.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present disclosure will be described with respect to particular embodiments and with reference to certain drawings, but the present disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the present disclosure.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate some circumstances and that the embodiments of the present disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under some circumstances and that the embodiments of the present disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device or arrangement comprising means A and B" should not be limited to devices or arrangements consisting only of components A and B. It means that with respect to the present disclosure, the only relevant components of the device or arrangement are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments of the present disclosure, various features of the present disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed present disclosure includes more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this present disclosure.

Furthermore, while some embodiments described herein include some but not other features included in other embodiments, combinations of features of different embodiments are meant to be within the scope of the present disclosure, and form different embodiments, as would be understood by those in the art. For example, in the following claims, any of the claimed embodiments can be used in any combination.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Where in embodiments of the present disclosure reference is made to flow focusing, reference is made to the 2D or 3D confinement of the flowing particles or cells in a channel or micro-channel. Flow focusing is an essential element for many microfluidic techniques, for example such as cell separation, enrichment or sorting.

In a first aspect, embodiments of the present disclosure relate to a focusing arrangement for focusing particles or cells in a flow, also referred to as flow focusing. Therefore, the arrangement includes at least one channel, and at least one acoustic confinement structure including acoustic field boundaries adapted for confining acoustic fields, at least partially, in the channel. The channel includes at least one particle confinement structure including particle flow boundaries, where the particle flow boundaries are different from the acoustic field boundaries. In embodiments according to the present disclosure, the channel is a microfluidic channel.

The focusing arrangement may be a microfluidic chip and the at least one channel may be a microchannel. The channel may be a channel in a chip. The channel may have any kind of cross-section (e.g. a rectangular cross section).

In embodiments of the present disclosure, the acoustic confinement structure is adapted for confining an acoustic field in a certain location. Focusing arrangements according to the present disclosure may include a transducer for generating an acoustic field. This generated acoustic field may be confined in the acoustic confinement structures. In embodiments of the present disclosure, one transducer, driven by one frequency, is sufficient for generating the acoustic fields within the acoustic confinement structures of the focusing arrangement. Thus, it is possible to obtain a target standing wave distribution in different channels. The reason therefore being that the channels have an individual acoustic confinement structure for confining an acoustic field resulting in an individual acoustic field distribution per channel. The standing wave distribution may, for example, be the same in different channels. In embodiments of the present disclosure, the acoustic fields of the acoustic confinement structures are controlled with regard to each other. The transducer may be a piezoelectric chip, which is used as an acoustic source for the focusing arrangement.

In embodiments of the present disclosure, the focusing arrangement may have a planar structure, where the channel is arranged in the planar structure. Hence, the primary direction of the focusing effect is the transversal direction.

In embodiments of the present disclosure, the transducer may be positioned against the surface of the planar focusing arrangement. In this case, acoustic waves may be launched orthogonal to the surface of the focusing arrangement. Only those waves which are propagated in other directions may result in acoustic waves in the acoustic confinement structure corresponding with the eigenmode of the acoustic confinement structure.

In embodiments of the present disclosure, the transducer may be positioned at the side of the planar focusing arrangement. In this case, transversal acoustic waves can be generated by the transducer; however, the side area is much smaller than the bottom area and therefore it may be less efficient to transfer acoustic wave energy through the side.

Therefore, in embodiments of the present disclosure, the transducer may be a micromachined ultrasonic transducer (e.g., capacitive micromachined ultrasonic transducer or piezoelectric micromachined ultrasonic transducer) located inside the microchannel. In this case, a microchannel may be formed on top of the manufactured micromachined ultrasonic transducer. This configuration could enable a higher acoustic energy delivery efficiency to the microchannel compared to the conventional configuration in which a transducer is placed outside the microchannel. Micromachined ultrasonic transducer is designed to launch a transversal acoustic wave in a more controlled fashion through the focusing arrangement.

Figure 19:
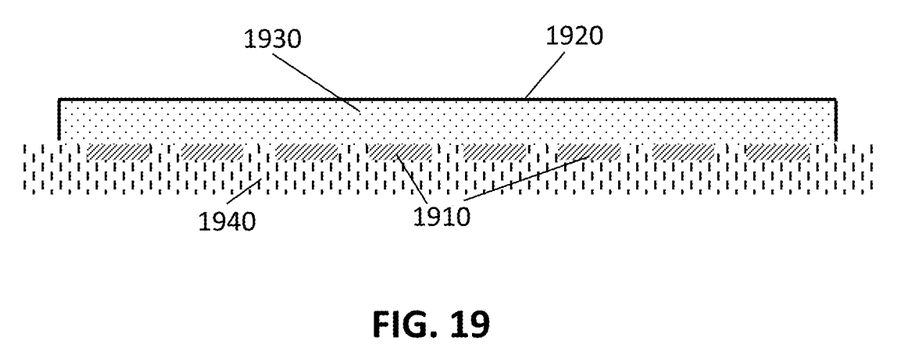
FIG. 19 illustrates a cross-section of a micromachined ultrasonic transducer designed to launch a transversal acoustic wave through a focusing arrangement, according to example embodiments.

FIG. 19 shows an example cross-section of a possible configuration of such a capacitive micromachined ultrasonic transducer or piezoelectric micromachined ultrasonic transducer 1910, where a microchannel 1930 is formed on top of the transducer 1910 and where an acoustic hard boundary 1920 (e.g., glass) is present as a wall of the microchannel 1930. Using such a transducer, a transversal standing wave acoustic field can be generated in the microchannel. The micromachined transducer may be manufactured on the surface of a silicon or glass substrate 1940, and a microchannel 1930 may be placed on top of it.

The generated field may be a bulk acoustic wave (BAW). Once the frequency of the acoustic vibration matches the resonance condition for the at least one channel, a standing wave can be generated transversally in each microfluidic channel.

The acoustic confinement structure may be global or local. In the case of local acoustic confinement structure, more than one of such a structure may be present for the same channel and/or, in case of more than one channel, each channel may have a different acoustic confinement structure.

Focusing arrangements according to the present disclosure may comprise multiple channels. The focusing arrangement is thereby constructed such that a focusing effect can be realized in every channel.

In some embodiments, even though the channels are on different positions of the chip, it may be possible to obtain sufficient standing waves for focusing in each channel by one operating frequency. This may be possible because of the plurality of acoustic confinement structures. In some embodiments, it may be possible to get the same standing wave and hence the same focusing effect in every channel.

Figure 1:
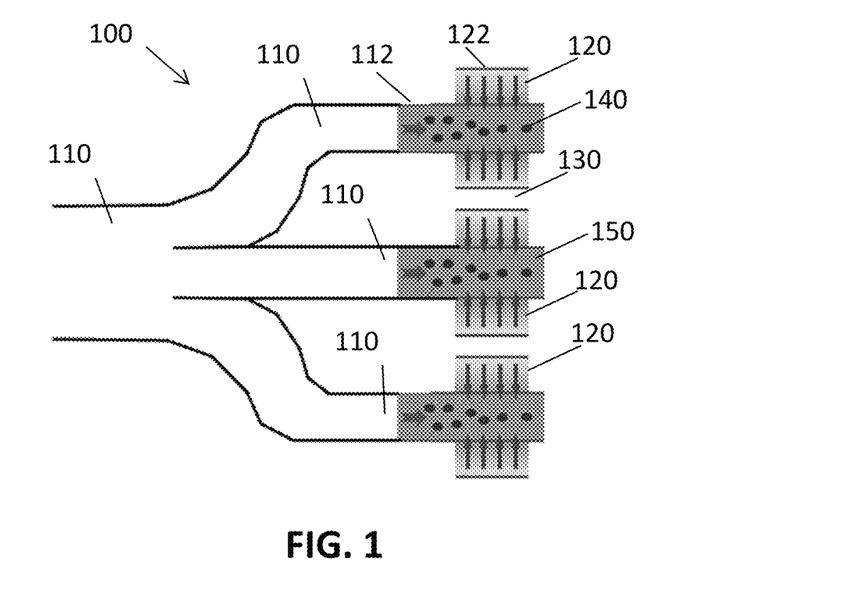
FIG. 1 illustrates a focusing arrangement including a parallel channel, according to example embodiments.

FIG. 1 shows a focusing arrangement 100 in accordance with embodiments of the present disclosure. Particles or cells 140 are respectively flowing through channels 110 in a liquid flow 150. In this example embodiment of the present disclosure the focusing arrangement 100 includes three parallel channels 110.

In FIG. 1, particle flow boundaries 112 correspond to the walls of channel 110. Moreover, the acoustic field boundaries 122 are different from the particle flow boundaries 112.

In such an embodiment with parallel channels, the acoustic field of one acoustic confinement structure 120 may interfere with the acoustic field of the other acoustic confinement structures 120. However, embodiments of the present disclosure may help cancel or at least suppress the acoustic wave going out of the acoustic confinement structure. Additionally or alternatively, such embodiments may help reduce coupling effects in a multichannel system with a plurality of acoustic confinement structures. Thus, a consistent focusing effect acting on the particles in all of the three channels is possible.

FIG. 1 shows acoustic barriers 130 present between the channels. Such an acoustic barrier can be a low acoustic impedance barrier, correspondingly a soft acoustic field boundary, or a high acoustic impedance barrier (a hard acoustic field boundary). These acoustic barriers may result in crosstalk between different channels being suppressed.

Figure 16:
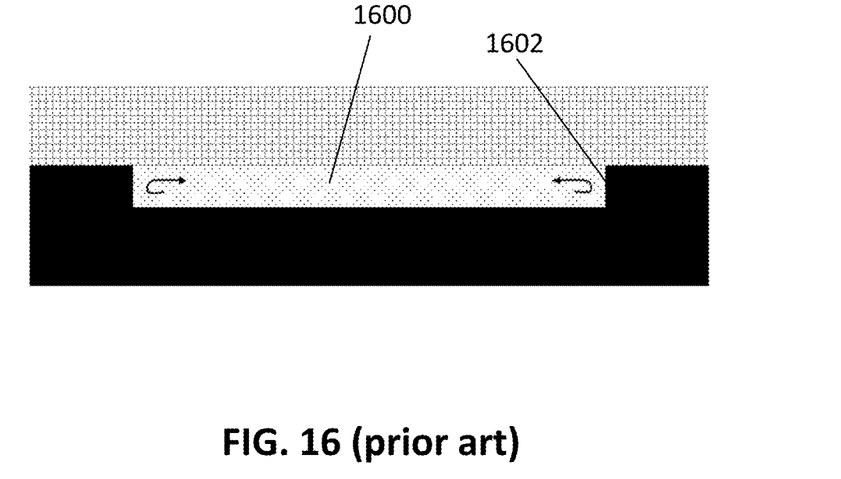
FIG. 16 illustrates a conventional channel, where the wall of the channel serves as an acoustic confinement structure and as a particle confinement structure.

FIG. 16 shows a conventional channel 1600 where the walls 1602 of the channel 1600 serve as acoustic field boundaries and as particle flow boundaries. In this example, the particle flow boundaries and the acoustic field boundaries are the same. The wall of the channel can for example be made of silicon or glass which has a large impedance mismatch with water.

Figure 17:
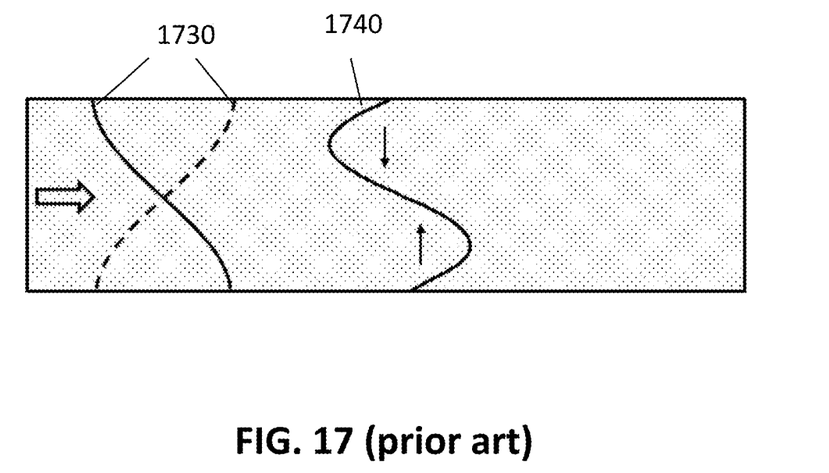
FIG. 17 illustrates the pressure field and acoustic radiation force in the channel of FIG. 16.

The pressure field 1730 and acoustic radiation force 1740 in a conventional channel are shown in FIG. 17.

Whereas in the conventional channel illustrated in FIG. 16 the particle confinement structure and the acoustic confinement structure are the same, being delimited by the channel 1600, in embodiments according to the present disclosure, the particle flow boundaries are different from the acoustic field boundaries.

Figure 2:
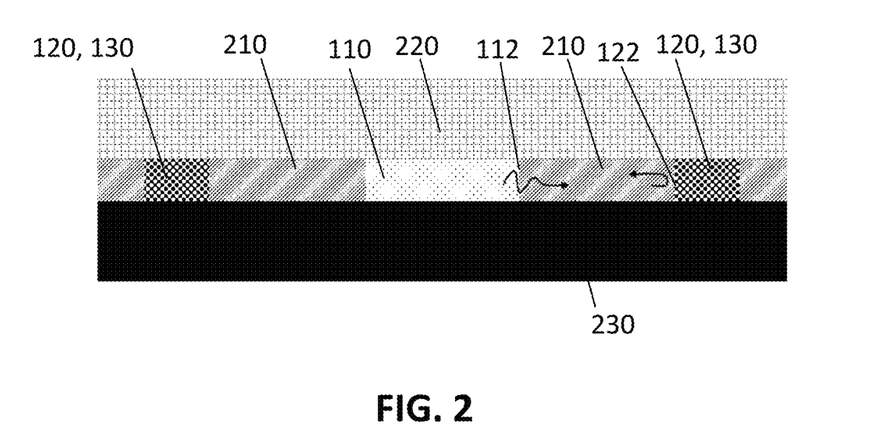
FIG. 2 illustrates one acoustic confinement structure of a focusing arrangement including matched walls and a barrier, according to example embodiments.

The particle confinement structure may for example be transparent for the acoustic field. Such a transparent layer 210 is used as material of the walls in the embodiment illustrated in FIG. 2. The transparent layer 210 forms the particle flow boundaries 112. Such a layer may for example be made of polydimethylsiloxane (PDMS) or photo-patternable adhesive (PA material). In that case most of the acoustic energy will be dissipated to the walls since they have an acoustic impedance close to the one of water. In embodiments according to the present disclosure, an acoustic barrier 130 may be added to form the acoustic field boundaries 112. An example embodiment of such a focusing arrangement is illustrated in FIG. 2. FIG. 2 schematically shows one acoustic confinement structure 120 of a focusing arrangement in accordance with embodiments of the present disclosure. In the embodiment illustrated in FIG. 2, the acoustic barriers 130 are used to confine the acoustic wave and thus are comprised in the acoustic confinement structure 120.

In embodiments according to the present disclosure, the acoustic confinement structures comprise may include acoustic field reflectors, absorbers or isolators.

Such a reflector may be an acoustic barrier. This acoustic barrier may be placed adjacent to the channel or in the neighborhood of the channel or may be a cavity used to reflect the traveling acoustic wave.

An acoustic channel 110 or cavity may, for example, be formed by etching a piece of silicon wafer or glass 230, and then bonding a covering 220 such as (e.g., a thin glass layers on top of it. The channel or cavity can be made by a thin layer of bonding polymers such as PDMS or PA material. These polymers have a similar acoustic impedance as water.

The acoustic barrier 130 can be either a soft barrier (in that case the acoustic impedance is much smaller than the matched walls) or a hard barrier (in that case the acoustic impedance is much larger than the matched walls). For instance, PDMS can be considered as the matched walls 210 and an air gap can be used as soft barrier 130. Due to the significant acoustic impedance mismatch between air and PDMS, most of the acoustic energy will be reflected by the air/PDMS interface 122 and a pressure node is formed. A standing wave can be generated between two air gaps at a certain frequency, correspondingly, a partial standing wave is obtained in the cavity.

In an example embodiment, the acoustic energy may be reflected on the barrier 130 at the acoustic field boundary 122. Hence, the acoustic energy may remain in the channel 110 as the waves do not continue into the chip, where they would be dissipated and attenuated. Additionally or alternatively, resonance power within the cavity may be increased by adding the barriers 130.

Figure 3:
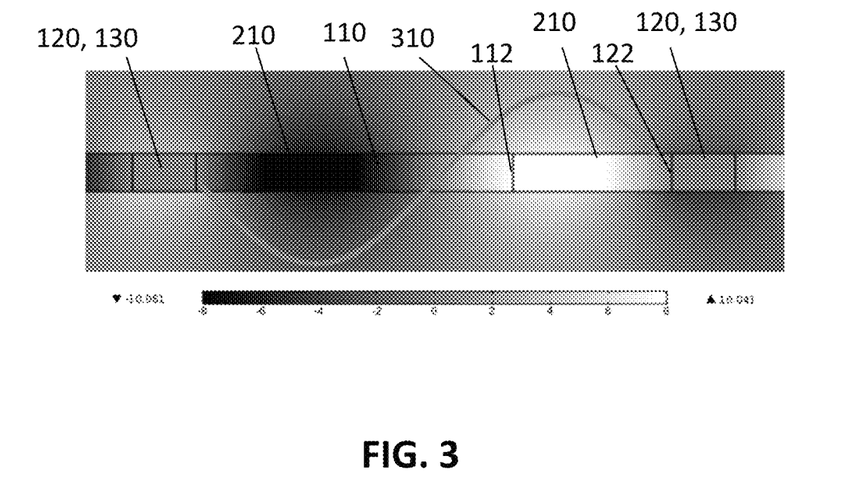
FIG. 3 illustrates the pressure field, in function of location, in an acoustic confinement structure of a focusing arrangement, according to example embodiments.

FIG. 3 shows the pressure field in function of the location in an acoustic confinement structure of a focusing arrangement, in accordance with embodiments of the present disclosure. The results are based on an Eigen frequency study in COMSOL (which is a finite element analysis solver and simulation software package). The unit of the Y-axis is in Pascale, however, more important is the distribution of the pressure field than the absolute value thereof. In embodiments according to the present disclosure, the waveform of the standing wave can be adjusted according to the location of air gaps and the width of PDMS layers (i.e. by the position of the acoustic field boundaries 122). As will be explained later, such a structure may be used when using consecutive acoustic confinement structures in a channel and thereby controlling the acoustic fields of the acoustic confinement structures with regard to each other, in accordance with embodiments of the present disclosure.

Figure 18:
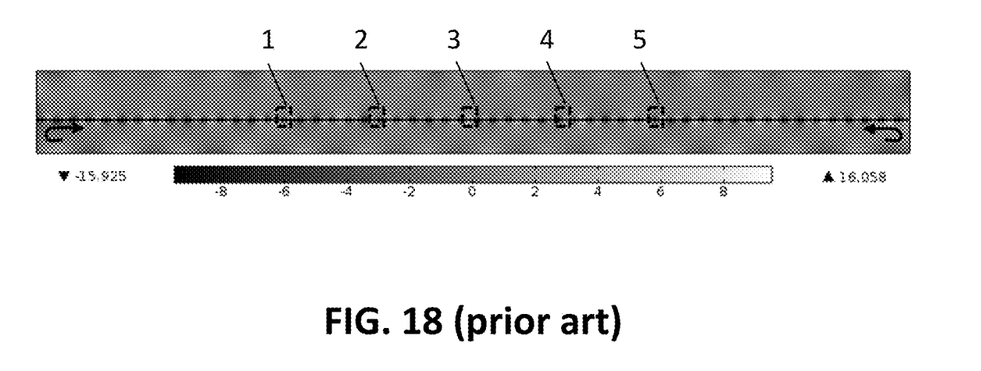
FIG. 18 illustrates a finite element analysis (COMSOL simulation) of the pressure field in a conventional five channel chip.

FIG. 18 shows a finite element analysis (COMSOL simulation) of the pressure field in a conventional five channel chip. It indicates that when the chip takes use of the transversal resonance mode, the pressure field is determined by the resonance of the whole chip. This is extremely evident when the wall of microchannel is made of polymers. The pressure field distribution in an individual channel highly relies on the location of the channel in the chip, which makes it is difficult to drive them together by using one frequency while also focusing the particles in the center of every channel. Therefore it is difficult to achieve a same standing wave distribution by just one eigenmode in a conventional five channel chip. If the center channel works at its resonance mode, the side channel is operated at a frequency (the driving frequency) shifted from its own resonance frequency. In reality, since each mode has a certain bandwidth, it is possible to achieve focusing in all of the channels by one frequency. But it also involves, in different channels, the acoustic radiation force and the corresponding focusing effect will being different.

In embodiments according to the present disclosure, this difference may be reduced by increasing the resonance of an individual channel. This could be done by providing acoustic confinement structures, which may be designed to tune the resonance for the different channels and hence make the coupling of the whole chip negligible.

Figure 4:
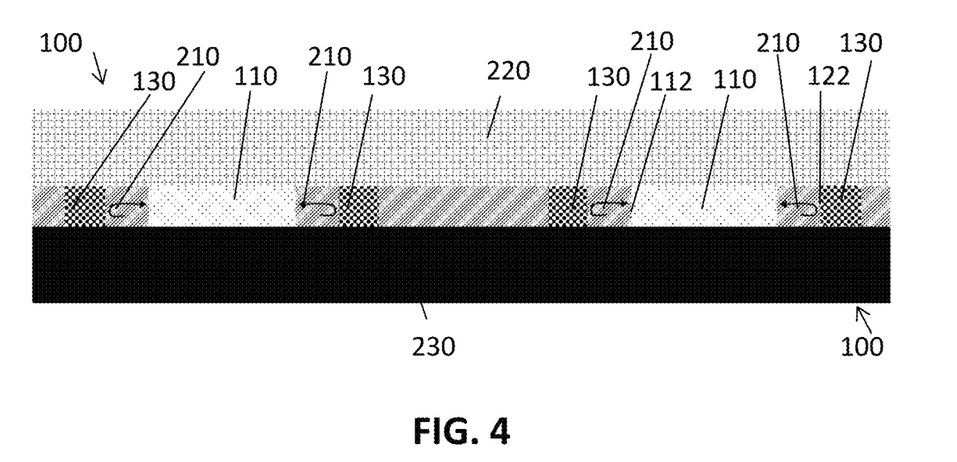
FIG. 4 illustrates a schematic cross-section of a focusing arrangement including two parallel channels, according to example embodiments.

In an example embodiment, the focusing arrangement comprises acoustic confinement structures of which the acoustic field boundaries are different from the particle flow boundaries. FIG. 4 shows a schematic cross-section of a focusing arrangement 100 including two parallel channels 110, in accordance with embodiments of the present disclosure. FIG. 4 shows that the acoustic barriers 130 can be used to suppress the acoustic coupling between different channels 110. The acoustic barriers 130 cut off the acoustic wave travelling in the thin layer of walls 210. Each channel 110 has a local resonance, and the resonance frequency is mainly determined by the space between the acoustic field boundaries 122 of the barriers 130. In this example embodiment of the present disclosure, only a slight frequency variation for different channels 110 at different locations is expected. This enables having multiple channel focusing by one operating frequency. In embodiments according to the present disclosure, this frequency variation may, for example, be smaller than 5%. Moreover, the acoustic field boundaries 122 may be different from the particle flow boundaries 112.

In embodiments of the present disclosure, the operating frequency is dominated by the dimension of the channel or by the acoustic confinement structures. This resonance frequency may depend on the position within the channel. If the wall is made by polymers, the resonance in the transversal direction is very weak. Later on, when the channel couples with the whole chip, the resonance frequency may shift significantly. The resonance frequency shift depends on the location of the channel in the chip. However, in embodiments of the present disclosure, where the acoustic confinement structures comprise barriers to strengthen the resonance, the resonance frequency is dominated by the space between barriers. The reason therefore being that the barriers have a larger impedance mismatch with the fluid (i.e., water) than the matched material of the walls of the channel. Therefore, there will be a stronger resonance for an individual channel.

In a focusing arrangement with a plurality of channels, a non-uniformity may exist between the resonance of the different channels which can be resolved using acoustic confinement structures in accordance with embodiments of the present disclosure.

This can be illustrated using the following example.

Consider a focusing arrangement in which the actual resonance frequency of a first channel is f0+f1, where f0 is the nominal frequency which is determined by the acoustic confinement structure at that position, and where f1 is the shifted frequency which is determined by the location of the channel in the chip (this shift originates from the coupling between the region within the acoustic confinement structure and the remaining part of the whole chip, which is expected from the coupled mode theory). The actual resonance frequency of the second channel is f0'+f2, the actual resonance frequency of the third channel is f0"+f3, and so on. The frequency shift f1, f2, f3 may depend on the location of the channel. Therefore, in embodiments of the present disclosure, the acoustic confinement structures may be dimensioned such that the actual resonance frequencies are adapted. In practice, f0, f0' and f0" may approximately equal for an identical space between acoustic field boundaries of an acoustic confinement structure. In embodiments of the present disclosure, the resonance of the channel can be strengthened, thereby reducing the coupling effect compared to the resonance effect (i.e., f1, f2 and f3 are negligible compared to f0, f0' and f0").

In an example embodiment, the uniformity of the acoustic field in each channel can be improved. This can be achieved by design of the acoustic field boundaries and is possible because the acoustic field boundaries are different from the particle flow boundaries.

In embodiments according to the present disclosure, the frequency of the standing wave on a certain location may be determined by the barriers around the channel and hence also the operating frequency may be determined by the barriers around the channel (i.e. by the position of the acoustic field boundaries). By increasing the barrier distance, the operating frequency will be lowered.

Focusing arrangements for which the acoustic field boundaries coincide with the particle flow boundaries may be confronted with the problem that the force by the acoustic field on the particles nearby the walls of the channel is limited. This is caused by a weak resonance of the acoustic field near the channel wall. Close to the channel walls the force on the particle may even approximate a zero force. This is the case in other focusing arrangements as illustrated in FIG. 17 which shows the pressure field 1730 and the acoustic radiation force 1740.

Figure 5:
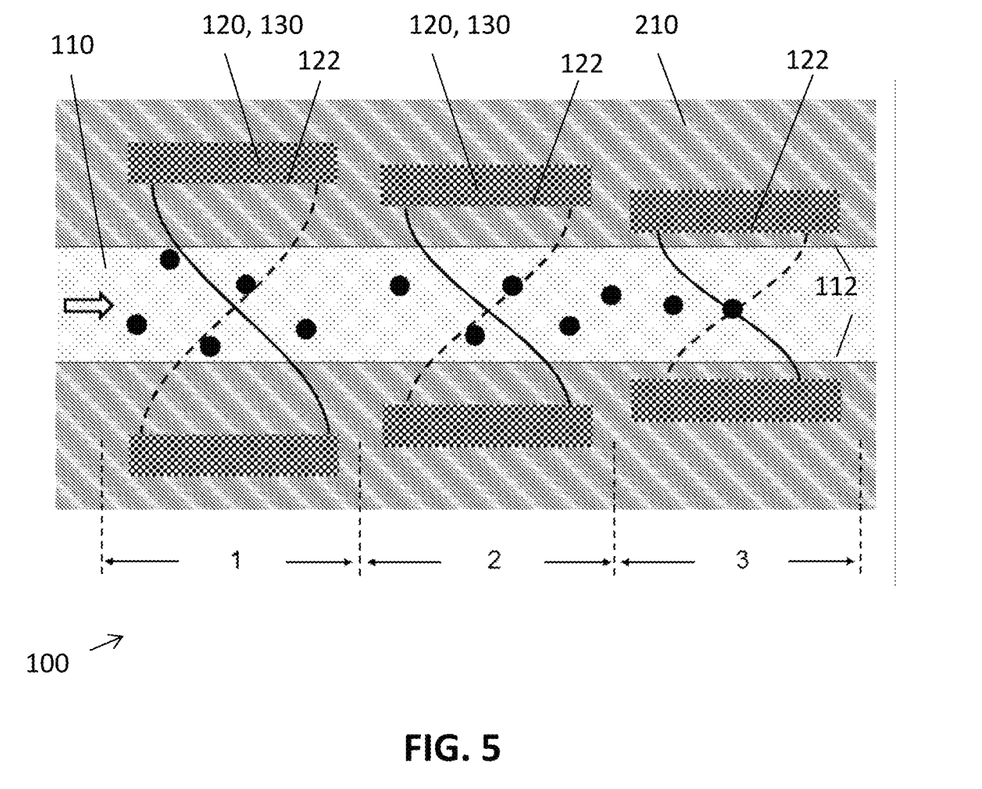
FIG. 5 illustrates a schematic drawing of a focusing arrangement including three consecutive local acoustic confinement structures, according to example embodiments.

FIG. 5 illustrates a channel 110 including consecutive acoustic confinement structures in accordance with embodiments of the present disclosure. Initially, the particles are randomly distributed in the channel. In zone 1, the acoustic confinement structure 120 including the barriers 130 (defining the acoustic field boundaries 122) is designed such that the acoustic radiation force is maximal at the wall of the channel. In zone 2, the acoustic confinement structure 120 is designed such that the acoustic radiation force forces the already centered particle closer to the center. Therefore, the barriers 130 may be positioned closer to the center than the barriers in zone 1, such that the maximum acoustic radiation force is located closer to the center. In zone 3, the acoustic confinement structure 120 is configured such that the acoustic confinement field focuses the particles even closer to the center. Therefore, a set of barriers 130 can be positioned closer to the center than the barriers in zone 2. Hence, the acoustic fields in the three different zones are controlled with regard to each other such that the particles are forced to the center of the channel. In this example, the particle flow boundaries 112 of the particle confinement structure correspond with the walls of the channel 110.

In embodiments according to the present disclosure, the position of the pressure node, this is the minimum (zero) amplitude point in the standing wave, of an acoustic confinement structure is not necessarily located at the center of the channel, which may enable the local trapping, observation and analysis of particles and cells.

Embodiments according to the present disclosure may include a particle confinement structure adapted for restricting the particle flow in the channel. In these embodiments, the particle confinement structure includes particle flow boundaries 112 different from the channel walls. The particle confinement structure may, for example, move the particles away from the channel wall. In embodiments of the present disclosure, the particle confinement structure may include the wall or part of the wall of the channel. In embodiments of the present disclosure, there may be more than one channel and micro structures may be present where the fluid can be guided. These micro structures may also include particle confinement structures adapted for restricting the flow of particles. The particle confinement structure may include a wall. It may also include an array of pillars that confine the particle flow. Such an array of pillars may confine the particle flow but not the liquid flow. In that case, the fluid can still flow along the wall but the particle cannot.

Figure 6:
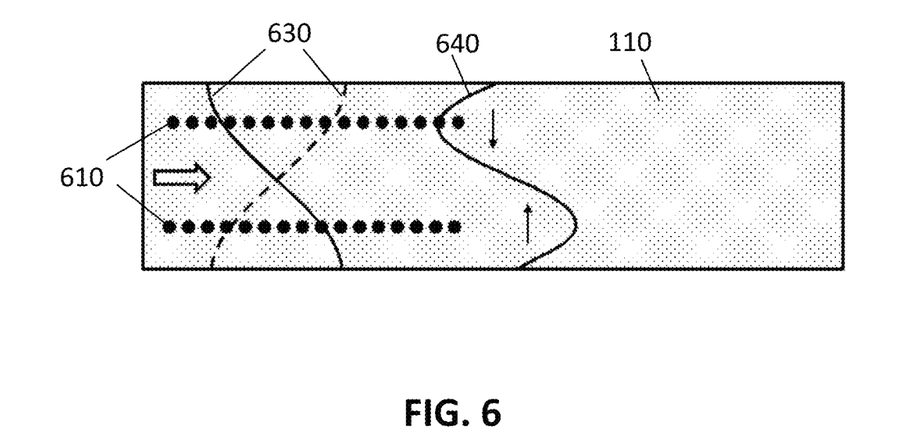
FIG. 6 illustrates a channel including a pillar array, according to example embodiments.

FIG. 6 shows a channel 110 including such a pillar array 610, in accordance with embodiments of the present disclosure. FIG. 6 shows the acoustic pressure field 630 (i.e. the standing wave) and the acoustic radiation force 640. In FIG. 6, the acoustic radiation force 640 on the particles is zero at the side walls but is already different from zero when away from the side walls. By introducing the micro pillars it is possible to speed up the acoustic focusing. When the dimension of micro pillars is much smaller than the acoustic wavelength, micro pillars are almost invisible to the acoustic field, and the target standing wave field can be maintained. Therefore, the pillars could be significantly smaller than the wavelength of the acoustic field. In an example embodiment, the pillars are as small as possible. This is limited by the minimum dimensions for the pillars in manufacturing. When, for example, working with PA material, the radius of the PA pillars can be as small as 5-10 µm. In embodiments according to the present disclosure, the space (or gap) between two pillars is between 2 and 100 µm, or possibly between 5 and 50 µm.

In embodiments of the present disclosure, the pillar array is designed such that particles might not be able to pass through the micro pillar array. These micro pillars can be used to limit and guide the movement region of particles.

Figure 7:
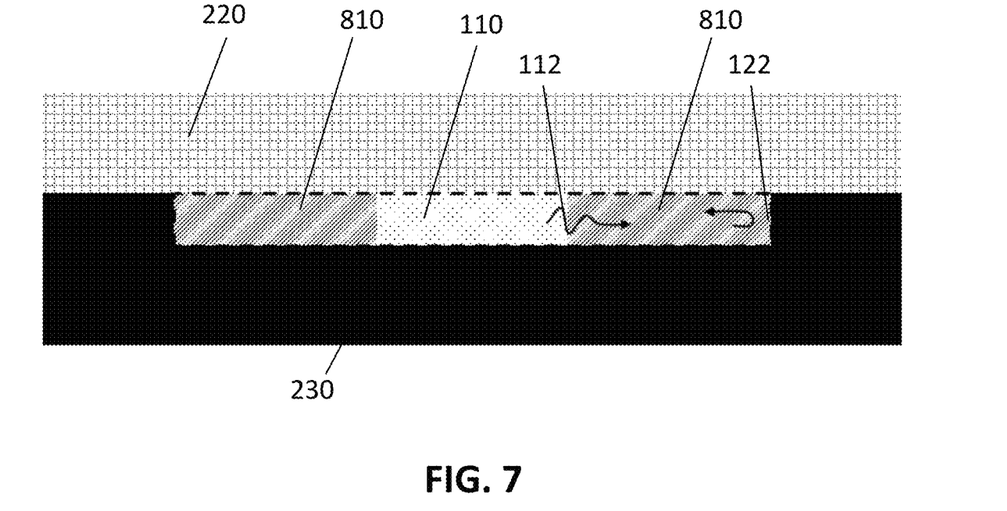
FIG. 7 illustrates the cross-section of a channel including an acoustic transparent layer, according to example embodiments.
Figure 8:
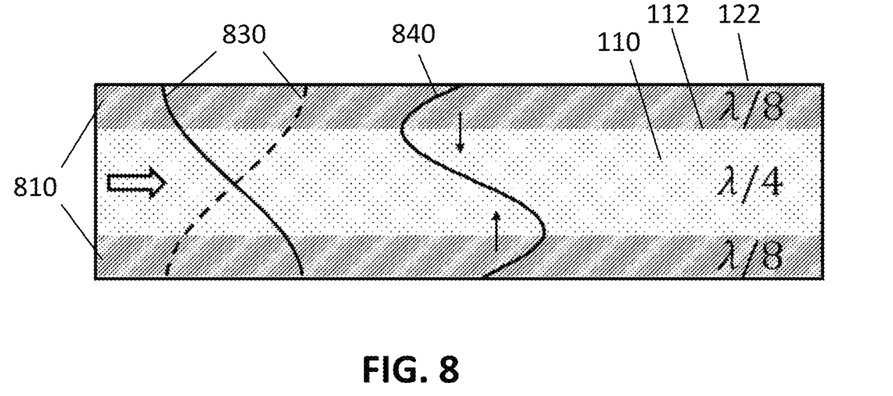
FIG. 8 illustrates the top view of a channel including an acoustic transparent layer, according to example embodiments.

In embodiments of the present disclosure, the channel may be a conventional hard wall channel (e.g. made of silicon or glass). In these embodiments, the channel may be partially filled with an acoustic transparent layer which serves as particle confinement structure. FIG. 7 and FIG. 8 show a channel comprising such an acoustic transparent layer 810. By introducing the acoustic transparent layer 810, the acoustic field boundaries 122 are different from the particle flow boundaries 112. The acoustic transparent layer thereby serves as a particle confinement structure. The region inside the dashed line in FIG. 7 is the conventional channel. The hard walls of the channel are the acoustic confinement structure.

In embodiments according to the present disclosure, an acoustic confinement structure is combined with a particle confinement structure. By combining a separate acoustic confinement structure and a particle confinement structure, the particle focusing can be enhanced.

FIG. 8 shows the pressure field 830 and the acoustic radiation force 840. In FIG. 8, the acoustic radiation force on the particles is zero at the acoustic field boundaries 122, but is already different from zero at the particle flow boundaries 112. By introducing the acoustic transparent layer 810, it is possible to speed up the acoustic focusing. In this example embodiment of the present disclosure, the focusing arrangement 100 is configured such that the width between the acoustic field boundaries 122 is half of the wavelength of the acoustic field and such that the acoustic transparent layers against the side wall have as width λ/8 and the remaining center of the channel 110, between the particle flow boundaries 112, has as width a quarter of the wavelength.

Focusing arrangements according to the present disclosure may include acoustic confinement structures in combination with particle confinement structures. Hence, the fluidic and acoustic conditions can be adjusted independently for improving the particle focusing performance. The acoustic confinement structure may include materials to define the acoustic field. These may be acoustically reflecting materials. In embodiments of the present disclosure, different resonators are present at different places of the channel as acoustic confinement elements. In these embodiments, the particle confinement structure may be the fluidic channel wall. In that case, the fluidic channel wall defines the liquid and the particle flow. Additionally, pillars may be added to confine the particle flow.

In an example embodiment, in a first section, the particles are pushed away from the channel walls towards the center of the channel.

Figure 9:
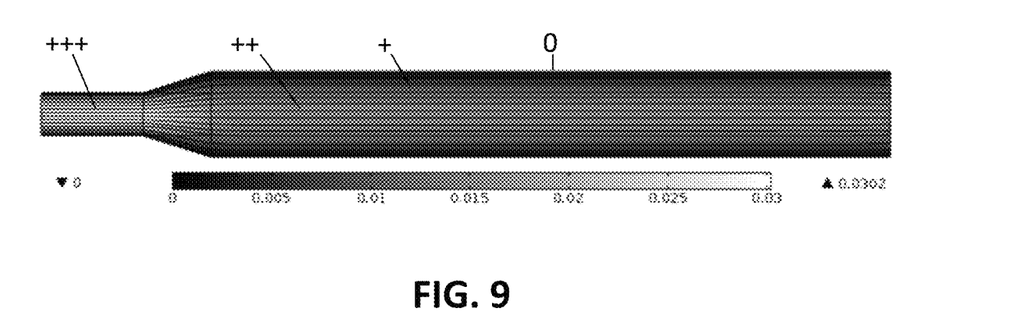
FIG. 9 illustrates the velocity of a laminar flow in a channel, according to example embodiments.

FIG. 9 shows the velocity of a laminar flow in a channel (in m/s). This and the following figures are to illustrate the distribution of the flow speed, the acoustic pressure, and the acoustic radiation force in a conventional channel compared to those in a channel, in accordance with embodiments of the present disclosure (the absolute values are not important). The highest speed is indicated with +++ and is achieved at the inlet of the channel. Lower speeds (++, +) are obtained later on in the channel and a zero speed (0) is obtained at the side walls of the channel. Particles will be randomly distributed across the width of the channel as a result of the laminar flow. According to the acoustic radiation force theory, those particles very close to the wall will receive zero radiation force, which will greatly lower the focusing speed.

Figure 10:
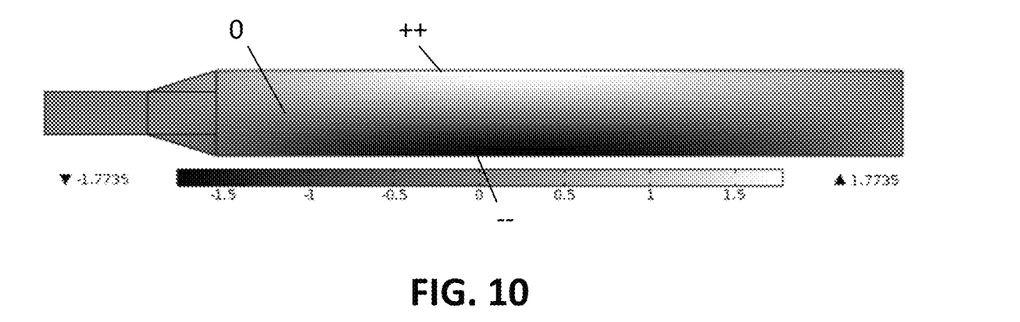
FIG. 10 illustrates the acoustic pressure field in a channel, according to example embodiments.

FIG. 10 shows the acoustic pressure field (indicated by ++, 0, --) in a channel (in Pa).

Figure 11:
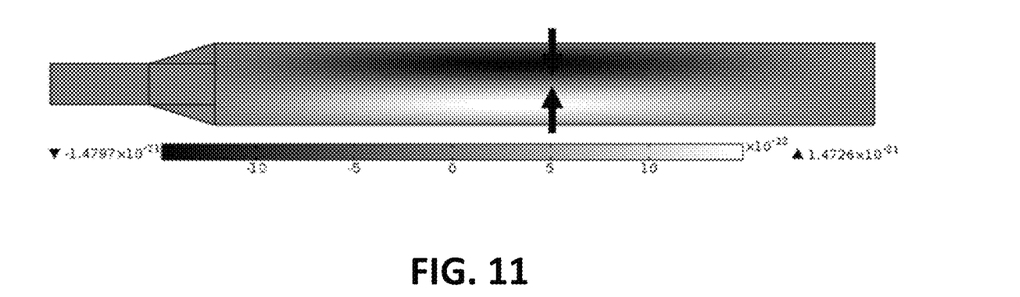
FIG. 11 illustrates the acoustic radiation force in a channel, according to example embodiments.

FIG. 11 shows the radiation force (in N) which is zero add the side walls of the channel.

Figure 12:
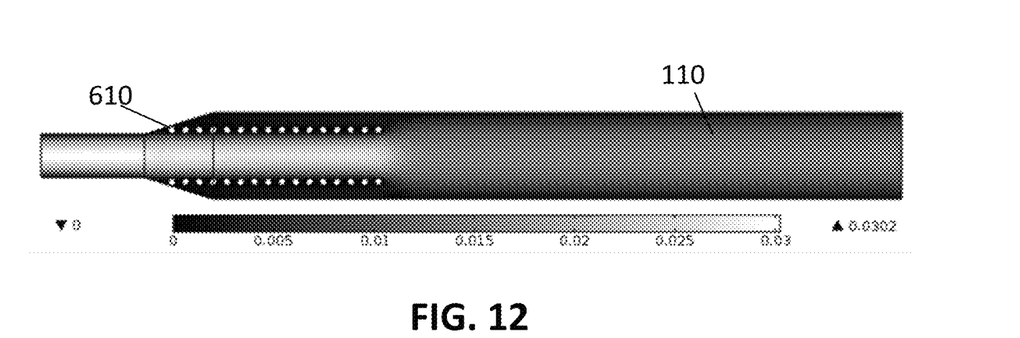
FIG. 12 illustrates the velocity of a laminar flow in a channel including micro pillars, according to example embodiments.

FIG. 12 shows the velocity (in m/s) of a laminar flow in a channel 110 including micro pillars 610, in accordance with embodiments of the present disclosure.

Figure 13:
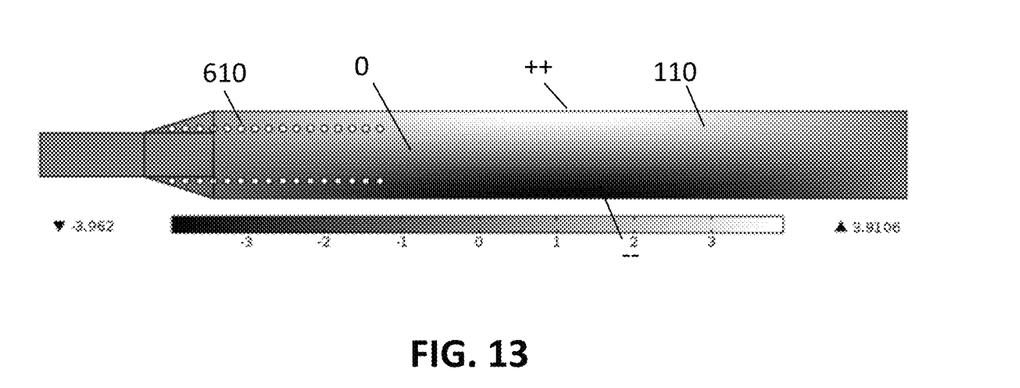
FIG. 13 illustrates the acoustic pressure field in a channel including micro pillars, according to example embodiments.

FIG. 13 shows the acoustic pressure field (in Pa) in a channel 110 including micro pillars 610 in accordance with embodiments of the present disclosure. As can be seen, the acoustic pressure fields with or without pillars are the same (FIG. 10 compared to FIG. 13).

Figure 14:
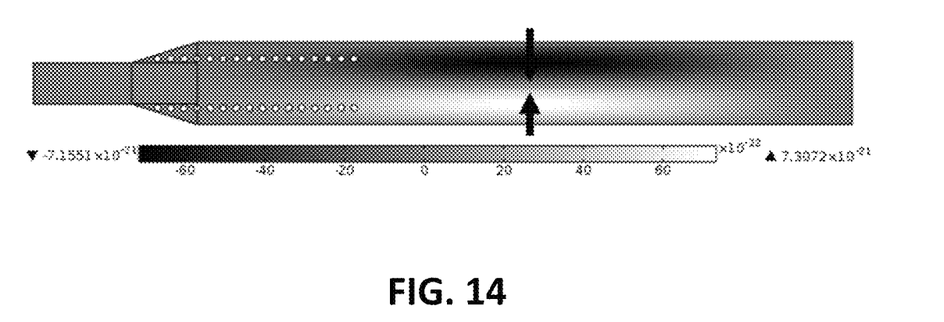
FIG. 14 illustrates the acoustic radiation force in a channel including micro pillars, according to example embodiments.

FIG. 14 shows the radiation force (in N) in a channel including micro pillars in accordance with embodiments of the present disclosure. As can be seen, the distribution of radiation forces with or without pillars is similar (FIG. 11 compared to FIG. 14).

Figure 15:
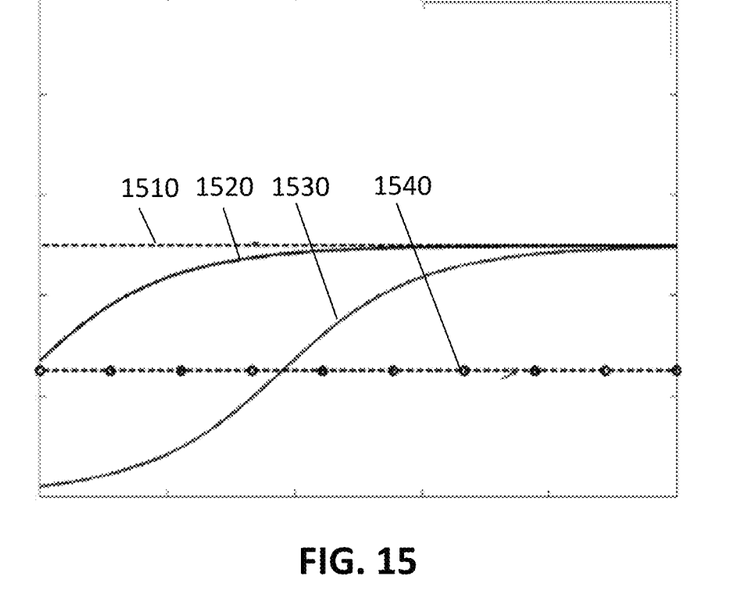
FIG. 15 illustrates an analytical simulation of transient particle trajectories in a channel with or without micro pillars, according to example embodiments.

FIG. 15 shows an analytical simulation of transient particle trajectories in a channel with or without micro pillars 610. The dashed horizontal line 1510 corresponds with the central line of the channel. Curve 1520 corresponds with the particle trajectory in function of time when starting at the micro pillars. The position of the micro pillars is indicated by line 1540. Curve 1530 corresponds with the particle trajectory in function of time when starting at a side wall of the channel. The x-axis is the time in seconds and the y-axis is the distance from one side wall of the channel. The transient trajectories of one 10 μm diameter polystyrene particle is shown. The start location is at the boundary of the channel 110 and at the boundary of micro pillars respectively. The simulation shows that in the presence of a pillar array particles take much shorter time to migrate to the center of the channel. In this example embodiment it takes about 0.02 s for a particle to migrate to the center when staring from the pillar array. When starting from the side wall this would be about 0.05 s.

The invention claimed is:

1. A focusing arrangement for focusing particles or cells in a flow, the focusing arrangement comprising:
   a first channel and a second channel positioned adjacent to the first channel, wherein the first channel and the second channel are configured to guide a first flow and a second flow of particles or cells, respectively, wherein each channel comprises a particle confinement structure, and wherein the particle confinement structure comprises a pair of inward-facing surfaces configured as particle flow boundaries within which the particles or cells flow and a pair of outward-facing surfaces opposite respective inward-facing surfaces; and
   an acoustic confinement structure that comprises an acoustic barrier, wherein the acoustic barrier is positioned in between adjacent outward-facing surfaces of particle confinement structures of the first channel and the second channel, to thereby configure the adjacent outward-facing surfaces as acoustic field boundaries within which acoustic fields are confined.

2. The focusing arrangement of claim 1, wherein the acoustic confinement structure further comprises a second acoustic barrier and a third acoustic barrier, wherein the second acoustic barrier and the third acoustic barrier are respectively positioned adjacent to non-adjacent outward-facing surfaces of particle confinement structures of the first channel and the second channel.

3. The focusing arrangement of claim 1, wherein the acoustic barrier is configured to reflect a traveling acoustic wave.

4. The focusing arrangement of claim 1, wherein the acoustic confinement structure is a first acoustic confinement structure, and wherein the channel comprises two consecutive acoustic confinement structures including the first acoustic confinement structure and a second acoustic confinement structure.

5. The focusing arrangement of claim 1, wherein the particle confinement structure comprises a pillar array.

6. The focusing arrangement of claim 1, wherein the particle confinement structure comprises an acoustic transparent layer.

7. The focusing arrangement of claim 1, further comprising a transducer configured to generate an acoustic wave between the acoustic field boundaries of the acoustic confinement structure.

8. A method comprising:
moving particles within a first channel and a second channel positioned adjacent to the first channel, wherein the first channel and the second channel are configured to guide the particles, wherein each channel comprises a particle confinement structure, and wherein the particle confinement structure comprises a pair of inward-facing surfaces configured as particle flow boundaries within which the particles flow and a pair of outward-facing surfaces opposite respective inward-facing surfaces; and
focusing the particles via an acoustic confinement structure that comprises an acoustic barrier, wherein the acoustic barrier is positioned in between adjacent outward-facing surfaces of particle confinement structures of the first channel and the second channel, to thereby configure the adjacent outward-facing surfaces as acoustic field boundaries within which acoustic fields are confined.

9. The method of claim 8, wherein the particles comprise first particles in the first channel and second particles in the second channel, and wherein the focusing comprises (i) focusing the first particles by applying a first acoustic field and (ii) focusing the second particles by applying a second acoustic field.

10. The method of claim 8, further comprising:
moving the particles in the first channel and the second channel away from the particle flow boundaries by applying a first acoustic field,
wherein the focusing comprises focusing the particles in the channel by applying a second acoustic field.

11. The method of claim 8, further comprising:
restricting flow of the particles in at least one of the first channel and the second channel before focusing the particles using an acoustic field.

12. The method of claim 11, wherein the flow of the particles is restricted using a pillar array.

13. The method of claim 11, wherein the flow of the particles is restricted using an acoustic transparent layer.

14. The method of claim 8, wherein the first channel, the second channel, and the acoustic confine structure are housed within a device.

15. The method of claim 14, wherein the acoustic confinement structure is configured to confine acoustic fields, at least partially, within the first channel and the second channel.

16. The method of claim 8, wherein the particles correspond to cells or bioparticles, and wherein the method is performed by a diagnostic device configured to focus flow of the cells or the bioparticles.

17. The method of claim 8, wherein the method is performed by an industrial inspection device configured to monitor a liquid flow comprising the particles.

18. A diagnostic device comprising:
a focusing arrangement for focusing bioparticles or cells in a flow, the focusing arrangement comprising:
a first channel and a second channel positioned adjacent to the first channel, wherein the first channel and the second channel are configured to guide a first flow and a second flow of particles or cells, respectively, wherein each channel comprises a particle confinement structure, and wherein the particle confinement structure comprises a pair of inward-facing surfaces configured as particle flow boundaries within which the particles or cells flow and a pair of outward-facing surfaces opposite respective inward-facing surfaces, and
an acoustic confinement structure that comprises an acoustic barrier, wherein the acoustic barrier is positioned in between adjacent outward-facing surfaces of particle confinement structures of the first channel and the second channel, to thereby configure the adjacent outward-facing surfaces as acoustic field boundaries within which acoustic fields are confined; and
a module configured to make a determination of one or more of a quality or quantity of the focused bioparticles or cells and provide an output based on the determination.

19. The diagnostic device of claim 18, wherein the acoustic confinement structure further comprises a second acoustic barrier and a third acoustic barrier, wherein the second acoustic barrier and the third acoustic barrier are respectively positioned adjacent to non-adjacent outward-facing surfaces of particle confinement structures of the first channel and the second channel particle confinement structures.

* * * * *